US008951575B2

(12) United States Patent
Kshirsagar et al.

(10) Patent No.: US 8,951,575 B2
(45) Date of Patent: Feb. 10, 2015

(54) MICROORGANISM CONCENTRATION AGENT AND METHOD OF MAKING (71) Applicant: 3M Innovative Properties Company, St. Paul, MN (US)

(72) Inventors: Manjiri T. Kshirsagar, Woodbury, MN (US); Tushar A. Kshirsagar, Woodbury, MN (US); Thomas E. Wood, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/023,782

(22) Filed: Sep. 11, 2013

(65) Prior Publication Data
US 2014/0011253 A1 Jan. 9, 2014

Related U.S. Application Data (62) Division of application No. 12/678,579, filed as application No. PCT/US2008/078575 on Oct. 2, 2008, now Pat. No. 8,546,100.

(60) Provisional application No. 60/977,200, filed on Oct. 3, 2007.

(51) Int. Cl.
*A61K 33/24* (2006.01)
*C12Q 1/02* (2006.01)
*C12Q 1/24* (2006.01)
*C12N 11/14* (2006.01)
*B01J 20/02* (2006.01)
*B01J 20/06* (2006.01)
*B01J 20/14* (2006.01)
*B01J 20/32* (2006.01)
*C12N 1/02* (2006.01)
*C12Q 1/04* (2006.01)

(52) U.S. Cl.
CPC .............. *C12N 11/14* (2013.01); *B01J 20/02* (2013.01); *B01J 20/06* (2013.01); *B01J 20/14* (2013.01); *B01J 20/3234* (2013.01); *B01J 20/3236* (2013.01); *C12N 1/02* (2013.01); *C12Q 1/04* (2013.01); *C12Q 1/24* (2013.01)
USPC .............................. 424/649; 435/29; 435/30

(58) Field of Classification Search
CPC .............. C12Q 1/04; C12Q 1/24; C12Q 1/10; C12Q 1/00; C12Q 1/02; C12Q 1/06; C12Q 1/28; C12Q 1/68; A61F 9/0017; A61F 9/00772; A61F 9/00781; C12N 1/02; C12N 11/14; G01N 1/405; G01N 2035/00326; G01N 33/56916; G01N 35/0092
See application file for complete search history.

(56) References Cited

U.S. PATENT DOCUMENTS

| | | |
|---|---|---|
| 3,912,593 A | 10/1975 | Barker |
| 4,046,712 A | 9/1977 | Cairns |
| 4,560,660 A | 12/1985 | Geirnaert |
| 4,618,525 A | 10/1986 | Chamberlain |
| 4,729,846 A | 3/1988 | Matsui |
| 5,238,812 A | 8/1993 | Coulter |
| 5,364,766 A | 11/1994 | Mach |
| 5,462,860 A | 10/1995 | Mach |
| 5,576,185 A | 11/1996 | Coulter |
| 5,759,403 A | 6/1998 | Clauss |
| 6,045,913 A | 4/2000 | Castle |
| 6,057,488 A | 5/2000 | Koper |
| 6,150,300 A | 11/2000 | Khare |
| 6,730,230 B2 | 5/2004 | Cook |
| 6,764,969 B1 | 7/2004 | Kuhn |
| 6,861,002 B2 | 3/2005 | Hughes |
| 7,074,916 B2 | 7/2006 | Bastian |
| 7,201,841 B2 | 4/2007 | Hughes |
| 7,422,868 B2 | 9/2008 | Fan |
| 7,431,904 B2 | 10/2008 | Høj |
| 8,057,688 B2 | 11/2011 | Nonninger |
| 2002/0077249 A1 | 6/2002 | Schlegel |
| 2003/0009014 A1 | 1/2003 | Chiou |
| 2003/0140785 A1 | 7/2003 | Koslow |
| 2003/0226443 A1 | 12/2003 | Rajagopalan |
| 2004/0127353 A1 | 7/2004 | Wu |
| 2004/0159605 A1 | 8/2004 | Hughes |
| 2004/0178142 A1 | 9/2004 | Koslow |
| 2004/0217061 A1 | 11/2004 | Corzani |
| 2005/0020449 A1 | 1/2005 | Blais |
| 2005/0095189 A1 | 5/2005 | Brey |

(Continued)

FOREIGN PATENT DOCUMENTS

| | | |
|---|---|---|
| CA | 2056167 | 11/1991 |
| EP | 0391608 | 3/1990 |

(Continued)

OTHER PUBLICATIONS

Ams et al., "Experimental measurements of the adsorption of *Bacillus subtilis* and *Pseudomonas mendocina* onto Fe-oxyhydroxide-coated and uncoated quartz grains" *Geomicrobiology Journal*, vol. 21, No. 8, pp. 511-519, ISSN: 0149-0451, XP008100501, Dec. 2004.

Berry, E. and Siragusa, G. "Hydroxyapatite Adherence as a Means to Concentrate Bacteria" *Applied and Environmental Microbiology*, pp. 4069-4074, Oct. 1997.

Brown et al., "Virus Removal by Diatomaceous-Earth Filtration—Part 1", *Journal American Water Works Association*, Denver, CO, vol. 66, No. 2, pp. 98-102, XP001013356, ISSN: 0003-150X, Jan. 1, 1974.

Bryant, T., "New UD Technology Removes Viruses From Drinking Water", *UDaily*, Office of Public Relations, University of Delaware, http://www.udel.edu/PR/UDaily/2007/feb/viruses022607.html, Feb. 26, 2007.

(Continued)

*Primary Examiner* — Debbie K Ware

(74) *Attorney, Agent, or Firm* — Adrian L. Pishko; Stephen L. Crooks

(57) ABSTRACT

A concentration agent for capture of microorganisms, including diatomaceous earth bearing, on at least a portion of its surface, a surface treatment comprising a surface modifier comprising titanium dioxide, fine-nanoscale gold or platinum, or a combination thereof, and methods for making the concentration agent.

14 Claims, 1 Drawing Sheet

(56) References Cited

U.S. PATENT DOCUMENTS

| | | | |
|---|---|---|---|
| 2006/0024776 | A1 | 2/2006 | McMillian |
| 2006/0144793 | A1 | 7/2006 | Dadachov |
| 2006/0188580 | A1 | 8/2006 | Sacks |
| 2006/0249465 | A1 | 11/2006 | Jin |
| 2006/0292555 | A1 | 12/2006 | Xu |
| 2007/0020649 | A1 | 1/2007 | Tseng |
| 2007/0212747 | A1 | 9/2007 | Browne |
| 2008/0166792 | A1 | 7/2008 | Attar |
| 2010/0190171 | A1 | 7/2010 | Kshirsagar |
| 2010/0209961 | A1 | 8/2010 | Kshirsagar |
| 2010/0247592 | A1 | 9/2010 | Kshirsagar |
| 2010/0248214 | A1 | 9/2010 | Kshirsagar |

FOREIGN PATENT DOCUMENTS

| | | |
|---|---|---|
| EP | 1524024 | 2/2010 |
| GB | 2228477 | 8/1990 |
| JP | 6-081595 | 10/1994 |
| JP | 2000-014380 | 1/2000 |
| JP | 2001-112497 | 4/2001 |
| JP | 2002-125695 | 5/2002 |
| JP | 2003-210158 | 7/2003 |
| JP | 2005-254123 | 9/2005 |
| WO | WO 02/49684 | 6/2002 |
| WO | WO 03/064330 | 8/2003 |
| WO | WO 2004/068511 | 8/2004 |
| WO | WO 2005/030382 | 4/2005 |
| WO | WO 2006/069712 | 7/2006 |
| WO | WO 2006/072944 | 7/2006 |
| WO | WO 2006/074126 | 7/2006 |
| WO | WO 2006/077020 | 7/2006 |
| WO | WO 2006/090375 | 8/2006 |
| WO | WO 2006/128187 | 11/2006 |
| WO | WO 2007/093808 | 8/2007 |
| WO | WO 2008/079800 | 7/2008 |
| WO | WO 2009/026035 | 2/2009 |

OTHER PUBLICATIONS

Chaudhuri et al., "Virus Removal by Diatomaceous Earth Filtration", *Journal of Environmental Engineering Division*, American Society of Civil Engineers, New York, NY, vol. 100, pp. 937-953, XP001013190, ISSN: 0090-3914, Aug. 1, 1974.

Collins et al., "Development of a rapid detection method for waterborne *Escherichia coli* O157:H7." XP002510684 Database accession No. PREV200300556872 abstract & Abstracts of the General Meeting of the American Society for Microbiology, vol. 103, 2003, pp. Q-496 URL, 103rd *American Society for Microbiology* General Meeting; Washington, DC, USA; May 18-22, 2003. ISSN: 1060-2011—Database BIOSIS [Online], Biosciences Information Service, Philadelphia, PA, US; 2003.

Cullison et al. "Magnetized Carbonyl Iron and Insoluble Zirconium Hydroxide Mixture Facilitates Bacterial Concentration and Separation from Nonfat Dry Milk", *Journal of Food Protection*, vol. 65, No. 11, pp. 1806-1810, Jun. 2002.

Farrah et al., "Adsorption of Viruses by Diatomaceous Earth Coated with Metallic Oxides and Metallic Peroxides", Wat. Sci. Tec., vol. 24, No. 2, pp. 235-240, 1991.

Farrah et al., "Adsorption of Viruses to Diatomaceous Earth Modified by in situ Precipitation of Metallic Salts", *Department of Microbiology and Cell Science*, University of Florida, vol. 34, No. 9, pp. 520-521, Jan. 1, 1988.

Farrah et al., "Use of Modified Diatomaceous Earth for Removal and Recovery of Viruses in Water" *Applied and Environmental Microbiology*, vol. 57, No. 9, pp. 2502-2506, XP001013212 ISSN: 0099-2240, Sep. 1, 1991.

Fass et al., "Silicates: non-specific adsorbents in purification of water from viruses", *Pub Med, NCBI, Dev. Biol. Stand*; vol. 46, pp. 91-96; 1980.

Fass et al., "Silicates as Nonspecific Adsorbents of Bacteriophage: a Model for Purification of Water from Viruses", Pub Med, NCBI, *Appl. Environ. Microbiol.*, vol. 39 (1), pp. 227-232; Jan. 1980.

Fu et al. "Anatase $TiO_2$ Nanocomposites for Antimicrobial Coatings", *J. Phys. Chem. B*, vol. 109, pp. 8889-8898 (2005).

Jiang et al., "Adsorption of Pseudomonoas Putida on Clay Minerals and Iron Oxide" *Colloids and Surfaces. B, Biointerfaces*, Elsevier, Amsterdam, NL, vol. 54, No. 2, pp. 217-221, XP005858731, ISSN: 0927-7765, Jan. 25, 2007.

Knapp et al., "The Effect of Distribution of Iron-oxyhydroxide Grain Coatings on the Transport of Bacterial Cells in Porous Media", *Environmental Geology (Berlin)*, vol. 33, No. 4, pp. 243-248, XP002510778, ISSN: 0943-0105, Mar. 1998.

Krack et al. "Effect of Growth Phase and Metabolic Activity on the Adhesion of *Escherichia coli* K-12 AB264 to Quartz and Lepidocrocite", *Geomicrobiology Journal*, vol. 24, No. 3-4, pp. 179-187, XP008100479, ISSN: 0149-0451, 2007.

Lucore et al., "Immobilization with Metal Hydroxides as a Means to Concentrate Food-Borne Bacteria for Detection by Cultural and Molecular Methods", *Applied and Environmental Microbiology*, vol. 66, No. 5, pp. 1769-1776, May 2000.

Lukasik et al., "Removal of Microorganisms from Water by Columns Containing Sand Coated with Ferric and Aluminum Hydroxides", *Wat. Res.*, vol. 33, No. 3, pp. 769-777, 1999.

Mills et al., "Effect of Solution Ionic Strength and Iron Coatings on Mineral Grains on the Sorption of Bacterial Cells to Quartz Sand", *Applied and Environmental Microbiology*, vol. 60, No. 9, pp. 3300-3306, XP002510777, ISSN: 0099-2240, 1994.

Rao et al., "Detection of Viruses in Drinking Water by Concentration on Magnetic Iron Oxide", *Applied and Environmental Microbiology*, vol. 42, No. 3, pp. 421-426, Sep. 1981.

Schindler et al., "Immobilization and Detection of Listeria Monocytogenes", *Applied and Environmental Microbiology*, vol. 72, No. 6, pp. 4426-4428, Jun. 2006.

Shah et al., "New Horizons in Purification of Liquids", *Soil and Water Pollution Monitoring, Protection and Remediation*, 3-23, pp. 369-386, 2006.

Stevens, K. and Jaykus, L-A, "Bacterial Separation and concentration from complex sample matrices: A Review" *Critical Reviews in Microbiology*, 30 (1), pp. 7-24, 2004.

Takeuchi et al., "High Dispersion Platinum Catalyst by RF Sputtering," *Journal of Catalysis*, vol. 83, pp. 477-479, 1983.

Taylor et al., "Effect of Food Matrix and Cell Growth on PCR-Based Detection of *Escherichia coli* O157:H7 in Ground Beef", *Journal of Food Protection*, vol. 68, No. 2, pp. 225-232, 2005.

Wegmann et al., "Modification of ceramic microfilters with colloidal zirconia to promote the adsorption of viruses from water", *Science Direct, Water Research* 42, pp. 1726-1734, 2008.

Zhu, et al., "Phase Transition between Nanostructures of Titanate and Titanium Cioxides via Simple Wet-Chemical Reactions", *J. Am. Chem. Soc.* (2005) vol. 127, 6730-6736.

MICROORGANISM CONCENTRATION AGENT AND METHOD OF MAKING

STATEMENT OF PRIORITY

This application is a Divisional patent application of U.S. patent application Ser. No. 12/678,579, now U.S. Pat. No. 8,546,100, which is a national stage filing under 35 U.S.C. 371 of PCT/US2008/078575 filed Oct. 10, 2008, which claims priority to U.S. Provisional Application No. 60/977,200 filed Oct. 3, 2007, the contents of which are hereby incorporated by reference.

FIELD

This invention relates to processes for capturing or concentrating microorganisms such that they remain viable for detection or assay. In other aspects, this invention also relates to concentration agents (and methods for their preparation) and diagnostic kits for use in carrying out such concentration processes.

BACKGROUND

Food-borne illnesses and hospital-acquired infections resulting from microorganism contamination are a concern in numerous locations all over the world. Thus, it is often desirable or necessary to assay for the presence of bacteria or other microorganisms in various clinical, food, environmental, or other samples, in order to determine the identity and/or the quantity of the microorganisms present.

Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Bacterial samples can be plated or cultured to increase the numbers of the bacteria in the sample to ensure an adequate level for detection, but the culturing step often requires substantial time and therefore can significantly delay the assessment results.

Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications.

Concentration methods that are not strain-specific have also been used (for example, to obtain a more general assessment of the microorganisms present in a sample). After concentration of a mixed population of microorganisms, the presence of particular strains can be determined, if desired, by using strain-specific probes.

Non-specific concentration or capture of microorganisms has been achieved through methods based upon carbohydrate and lectin protein interactions. Chitosan-coated supports have been used as non-specific capture devices, and substances (for example, carbohydrates, vitamins, iron-chelating compounds, and siderophores) that serve as nutrients for microorganisms have also been described as being useful as ligands to provide non-specific capture of microorganisms.

Various inorganic materials (for example, hydroxyapatite and metal hydroxides) have been used to non-specifically bind and concentrate bacteria. Physical concentration methods (for example, filtration, chromatography, centrifugation, and gravitational settling) have also been utilized for non-specific capture, with and/or without the use of inorganic binding agents. Such non-specific concentration methods have varied in speed, cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness.

SUMMARY

Thus, we recognize that there is an urgent need for processes for rapidly detecting pathogenic microorganisms. Such processes will preferably be not only rapid but also low in cost, simple (involving no complex equipment or procedures), and/or effective under a variety of conditions (for example, with varying types of sample matrices, varying bacterial loads, and varying sample volumes).

Briefly, in one aspect, this invention provides a process for non-specifically concentrating the strains of microorganisms (for example, strains of bacteria, fungi, yeasts, protozoans, viruses (including both non-enveloped and enveloped viruses), and bacterial endospores) present in a sample, such that the microorganisms remain viable for the purpose of detection or assay of one or more of the strains. The process comprises (a) providing a concentration agent (preferably, a particulate concentration agent) that comprises diatomaceous earth bearing, on at least a portion of its surface, a surface treatment comprising a surface modifier comprising titanium dioxide, fine-nanoscale gold or platinum, or a combination thereof; (b) providing a sample (preferably, in the form of a fluid) comprising at least one microorganism strain; and (c) contacting (preferably, by mixing) the concentration agent with the sample such that at least a portion of the at least one microorganism strain is bound to or captured by the concentration agent. Preferably, the process further comprises detecting the presence of the at least one bound microorganism strain (for example, by culture-based, microscopy/imaging, genetic, bioluminescence-based, or immunologic detection methods) and/or segregating (preferably, by gravitational settling) the resulting microorganism-bound concentration agent. The process can optionally further comprise separating the resulting segregated concentration agent from the sample.

The process of the invention does not target a specific microorganism strain. Rather, it has been discovered that certain relatively inexpensive, inorganic materials can be surprisingly effective in capturing a variety of microorganisms. Such materials can be used to concentrate the microorganism strains present in a sample (for example, a food sample) in a non-strain-specific manner, so that one or more of the microorganism strains (preferably, one or more strains of bacteria) can be more easily and rapidly assayed.

The process of the invention is relatively simple and low in cost (requiring no complex equipment or expensive strain-specific materials) and can be relatively fast (preferred embodiments capturing at least about 70 percent (more preferably, at least about 80 percent; most preferably, at least about 90 percent) of the microorganisms present in a sample in less than about 30 minutes, relative to a corresponding control sample without concentration agent). In addition, the process can be effective with a variety of microoganisms (including pathogens such as both gram positive and gram negative bacteria) and with a variety of samples (different sample matrices and, unlike at least some prior art methods, even samples having low microorganism content and/or large volumes). Thus, at least some embodiments of the process of the invention can meet the above-cited urgent need for low-cost, simple processes for rapidly detecting pathogenic microorganisms under a variety of conditions.

In another aspect, the invention also provides a diagnostic kit for use in carrying out the process of the invention, the kit comprising (a) a concentration agent (preferably, a particulate concentration agent) that comprises diatomaceous earth bearing, on at least a portion of its surface, a surface treatment comprising a surface modifier comprising titanium dioxide, fine-nanoscale gold or platinum, or a combination thereof; and (b) a testing container (preferably, a sterile testing container) for use in carrying out the process of the invention. Preferably, the diagnostic kit further comprises one or more components selected from microorganism culture media, lysis reagents, buffers, genetic detection assay components, bioluminescence detection assay components, instructions for carrying out the process, and combinations thereof.

In yet another aspect, the invention provides a concentration agent comprising titanium dioxide, fine-nanoscale gold or platinum, or a combination thereof on a particulate support selected from diatomaceous earth, metal oxide-modified diatomaceous earth, and combinations thereof.

In still another aspect, the invention provides a process for preparing a concentration agent comprising (a) providing a particulate support selected from diatomaceous earth, metal oxide-modified diatomaceous earth, and combinations thereof; and (b) depositing fine-nanoscale gold or platinum on the support by physical vapor deposition.

In yet another aspect, the invention provides a process for preparing a concentration agent comprising (a) providing a particulate support selected from diatomaceous earth, metal oxide-modified diatomaceous earth, and combinations thereof; (b) providing a hydrolyzable titanium dioxide precursor compound; (c) combining the support and the compound; and (d) hydrolyzing the compound so as to deposit titanium dioxide on the support.

BRIEF DESCRIPTION OF DRAWING

These and other features, aspects, and advantages of the present invention will become better understood with regard to the following description, appended claims, and accompanying drawing, wherein:

These figures, which are idealized, are not drawn to scale and are intended to be merely illustrative and nonlimiting.

DETAILED DESCRIPTION

Definitions

As used in this patent application:

"sample" means a substance or material that is collected (for example, to be analyzed);

"sample matrix" means the components of a sample other than microorganisms;

"detection" means the identification of at least a component of a microorganism, which thereby determines that the microorganism is present;

"genetic detection" means the identification of a component of genetic material such as DNA or RNA that is derived from a target microorganism;

"immunologic detection" means the identification of an antigenic material such as a protein or a proteoglycan that is derived from a target microorganism;

"microorganism" means any cell having genetic material suitable for analysis or detection (including, for example, bacteria, yeasts, viruses, and bacterial endospores);

"microorganism strain" means a particular type of microorganism that is distinguishable through a detection method (for example, microorganisms of different genera, of different species within a genera, or of different isolates within a species); and "target microorganism" means any microorganism that is desired to be detected.

Concentration Agent

Concentration agents suitable for use in carrying out the process of the invention include those that comprise diatomaceous earth bearing, on at least a portion of its surface, a surface treatment comprising a surface modifier comprising titanium dioxide, fine-nanoscale gold or platinum, or a combination thereof. Concentration or capture using such concentration agents is generally not specific to any particular strain, species, or type of microorganism and therefore provides for the concentration of a general population of microorganisms in a sample. Specific strains of microorganisms can then be detected from among the captured microorganism population using any known detection method with strain-specific probes. Thus, the concentration agents can be used for the detection of microbial contaminants or pathogens (particularly food-borne pathogens such as bacteria) in clinical, food, environmental, or other samples.

In carrying out the process of the invention, the concentration agents can be used in any form that is amenable to sample contact and microorganism capture (for example, in particulate form or applied to a support such as a dipstick, film, filter, tube, well, plate, beads, membrane, or channel of a microfluidic device, or the like). Preferably, the concentration agents are used in particulate form.

When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). At least some of the concentration agents used in carrying out the process of the invention have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged. Preferably, the concentration agents have a negative zeta potential at a pH of about 7 (more preferably, a zeta potential in the range of about −5 millivolts to about −20 millivolts at a pH of about 7; even more preferably, a zeta potential in the range of about −8 millivolts to about −19 millivolts at a pH of about 7; most preferably, a zeta potential in the range of about −10 millivolts to about −18 millivolts at a pH of about 7).

Thus, it has been discovered that concentration agents comprising certain types of surface-treated or surface-modified diatomaceous earth (namely, bearing a surface treatment comprising a surface modifier comprising titanium dioxide, fine-nanoscale gold or platinum, or a combination thereof) can be surprisingly more effective than untreated diatomaceous earth in concentrating microorganisms. The surface treatment preferably further comprises a metal oxide selected from ferric oxide, zinc oxide, aluminum oxide, and the like, and combinations thereof (more preferably, ferric oxide).

Although noble metals such as gold have been known to exhibit antimicrobial characteristics, the gold-containing concentration agents used in the process of the invention surprisingly can be effective not only in concentrating the microorganisms but also in leaving them viable for purposes of detection or assay.

Useful surface modifiers include fine-nanoscale gold; fine-nanoscale platinum; fine-nanoscale gold in combination with at least one metal oxide (preferably, titanium dioxide, ferric oxide, or a combination thereof); titanium dioxide; titanium dioxide in combination with at least one other (that is, other than titanium dioxide) metal oxide; and the like; and combinations thereof. Preferred surface modifiers include fine-nanoscale gold; fine-nanoscale platinum; fine-nanoscale gold in combination with at least ferric oxide or titanium dioxide; titanium dioxide; titanium dioxide in combination with at least ferric oxide; and combinations thereof.

More preferred surface modifiers include fine-nanoscale gold; fine-nanoscale platinum; fine-nanoscale gold in combination with ferric oxide or titanium dioxide; titanium dioxide; titanium dioxide in combination with ferric oxide; and combinations thereof (even more preferably, fine-nanoscale gold; fine-nanoscale gold in combination with ferric oxide or titanium dioxide; titanium dioxide in combination with ferric oxide; and combinations thereof). Fine-nanoscale gold, fine-nanoscale gold in combination with ferric oxide or titanium dioxide, and combinations thereof are most preferred.

Gold and/or Platinum

The concentration agents comprising fine-nanoscale gold or platinum can be prepared by depositing gold or platinum on diatomaceous earth by physical vapor deposition (optionally, by physical vapor deposition in an oxidizing atmosphere). As used herein, the term "fine-nanoscale gold or platinum" refers to gold or platinum bodies (for example, particles or atom clusters) having all dimensions less than or equal to 5 nanometers (nm) in size. Preferably, at least a portion of the deposited gold or platinum has all dimensions (for example, particle diameter or atom cluster diameter) in the range of up to (less than or equal to) about 10 nm in average size (more preferably, up to about 5 nm; even more preferably, up to about 3 nm).

In most preferred embodiments, at least a portion of the gold is ultra-nanoscale (that is, having at least two dimensions less than 0.5 nm in size and all dimensions less than 1.5 nm in size). The size of individual gold or platinum nanoparticles can be determined by transmission electron microscopy (TEM) analysis, as is well known in the art.

The amount of gold or platinum provided on the diatomaceous earth can vary over a wide range. Since gold and platinum are expensive, it is desirable not to use more than is reasonably needed to achieve a desired degree of concentration activity. Additionally, because nanoscale gold or platinum can be highly mobile when deposited using PVD, activity can be compromised if too much gold or platinum is used, due to coalescence of at least some of the gold or platinum into large bodies.

For these reasons, the weight loading of gold or platinum on the diatomaceous earth preferably is in the range of about 0.005 (more preferably, 0.05) to about 10 weight percent, more preferably about 0.005 (even more preferably, 0.05) to about 5 weight percent, and even more preferably from about 0.005 (most preferably, 0.05) to about 2.5 weight percent, based upon the total weight of the diatomaceous earth and the gold or platinum.

Gold and platinum can be deposited by PVD techniques (for example, by sputtering) to form concentration-active, fine-nanoscale particles or atom clusters on a support surface. It is believed that the metal is deposited mainly in elemental form, although other oxidation states may be present.

In addition to gold and/or platinum, one or more other metals can also be provided on the same diatomaceous earth supports and/or on other supports intermixed with the gold- and/or platinum-containing supports. Examples of such other metals include silver, palladium, rhodium, ruthenium, osmium, copper, iridium, and the like, and combinations thereof. If used, these other metals can be co-deposited on a support from a target source that is the same or different from the gold or platinum source target that is used. Alternatively, such metals can be provided on a support either before or after the gold and/or platinum is deposited. Metals requiring a thermal treatment for activation advantageously can be applied to a support and heat treated before the gold and/or platinum is deposited.

Physical vapor deposition refers to the physical transfer of metal from a metal-containing source or target to a support medium. Physical vapor deposition can be viewed as involving atom-by-atom deposition, although in actual practice the metal can be transferred as extremely fine bodies constituting more than one atom per body. The deposited metal can interact with the surface of the support medium physically, chemically, ionically, and/or otherwise.

Physical vapor deposition preferably occurs under temperature and vacuum conditions in which the metal is quite mobile and will tend to migrate on the surface of the support medium until immobilized in some fashion (for example, by adhering to a site on or very near the support surface). Sites of adhering can include defects such as surface vacancies, structural discontinuities such as steps and dislocations, and interfacial boundaries between phases or crystals or other metal species such as small metal clusters. Metal deposited by PVD apparently is sufficiently immobilized that the metal can retain a high level of activity. In contrast, conventional methodologies often allow the metal to coalesce into such large bodies that activity can be compromised or even lost.

Physical vapor deposition can be carried out in various different ways. Representative approaches include sputter deposition (preferred), evaporation, and cathodic arc deposition. Any of these or other PVD approaches can be used in preparing the concentration agents used in carrying out the process of the invention, although the nature of the PVD technique can impact the resulting activity.

For example, the energy of the physical vapor deposition technique can impact the mobility of the deposited metal and hence its tendency to coalesce. Higher energy tends to correspond to an increased tendency of the metal to coalesce. Increased coalescence, in turn, tends to reduce activity. Generally, the energy of the depositing species is lowest for evaporation, higher for sputter deposition (which can include some ion content in which a small fraction of the impinging metal species are ionized), and highest for cathodic arc deposition (which can include several tens of percents of ion content). Accordingly, if a particular PVD technique yields deposited metal that is more mobile than desired, it can be useful to use a PVD technique of lesser energy instead.

Physical vapor deposition preferably is performed while the support medium to be treated is being well-mixed (for example, tumbled, fluidized, milled, or the like) to ensure adequate treatment of support surfaces. Methods of tumbling particles for deposition by PVD are described in U.S. Pat. No. 4,618,525 (Chamberlain et al.), the descriptions of which are incorporated herein by reference.

When carrying out PVD on fine particles or fine particle agglomerates (for example, less than about 10 micrometers in average diameter), the support medium is preferably both mixed and comminuted (for example, ground or milled to some degree) during at least a portion of the PVD process. This can assist in maintaining the separation and free flow of the particles or agglomerates during the deposition. In the case of fine particles or fine particle agglomerates, it can be advantageous for the mixing of the particles to be as vigorous and rapid as possible while still retaining controlled deposition of the metal.

PVD can be carried out by using any of the types of apparatus that are now used or hereafter developed for this purpose. A preferred apparatus 10 is shown, however, in FIGS. 1 and 2. The apparatus 10 includes a housing 12 defining a vacuum chamber 14 containing a particle agitator 16. The housing 12, which can be made from an aluminum alloy if desired, is a vertically oriented hollow cylinder (for example, 45 cm high and 50 cm in diameter). The base 18 contains a port 20 for a high vacuum gate valve 22 followed by a six-inch diffusion pump 24 as well as a support 26 for the particle agitator 16. The vacuum chamber 14 is capable of being evacuated to background pressures in the range of $10^{-6}$ Torr.

Figure 1:
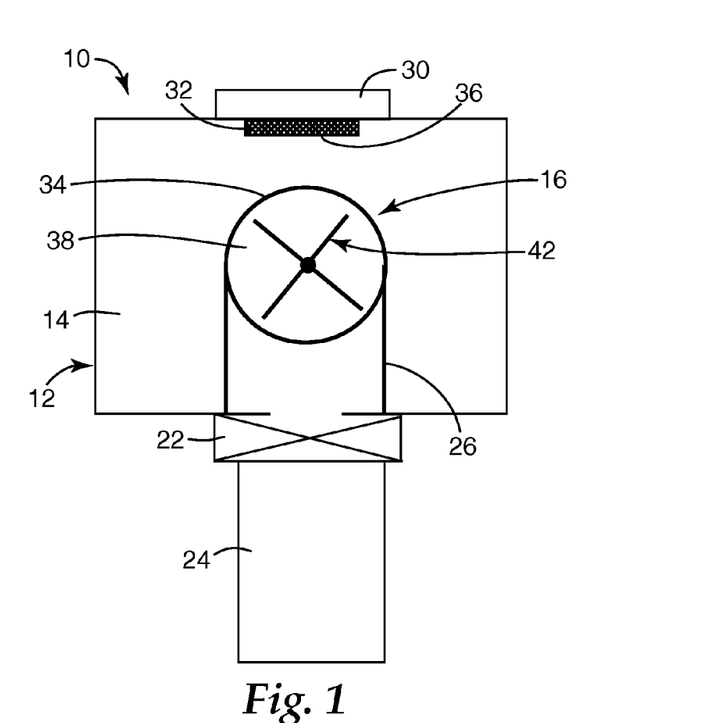
FIG. 1 shows, in side sectional view, an apparatus that was used in preparing concentration agents for use in carrying out the embodiments of the process of the invention described in the examples section below.
Figure 2:
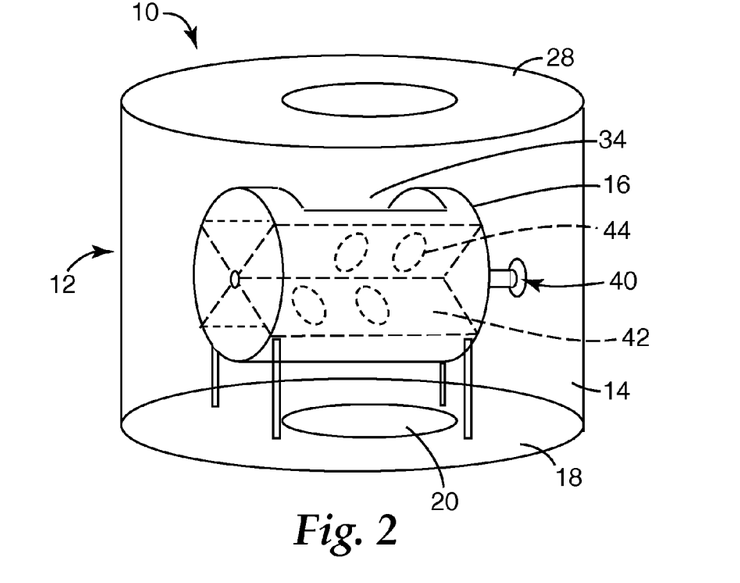
FIG. 2 shows, in perspective view, the apparatus of FIG. 1.

The top of the housing 12 includes a demountable, rubber L-gasket-sealed plate 28 that is fitted with an external mount, three-inch diameter direct current (dc) magnetron sputter deposition source 30 (a US Gun II, US, INC., San Jose, Calif.). Into the sputter deposition source 30 is fastened a gold or platinum sputter target 32 (for example, 7.6 cm (3.0 inch) diameter×0.48 cm (3/16 inch) thick). The sputter deposition source 30 is powered by an MDX-10 Magnetron Drive (Advanced Energy Industries, Inc, Fort Collins, Colo.) fitted with a Sparc-le 20 arc suppression system (Advanced Energy Industries, Inc, Fort Collins, Colo.).

The particle agitator 16 is a hollow cylinder (for example, 12 cm long×9.5 cm diameter horizontal) with a rectangular opening 34 (for example, 6.5 cm×7.5 cm). The opening 34 is positioned about 7 cm directly below the surface 36 of the sputter target 32, so that sputtered metal atoms can enter the agitator volume 38. The agitator 16 is fitted with a shaft 40 aligned with its axis. The shaft 40 has a rectangular cross section (for example, 1 cm×1 cm) to which are bolted four rectangular blades 42 which form an agitation mechanism or paddle wheel for the support particles being tumbled. The blades 42 each contain two holes 44 (for example, 2 cm diameter) to promote communication between the particle volumes contained in each of the four quadrants formed by the blades 42 and particle agitator 16. The dimensions of the blades 42 are selected to give side and end gap distances of either 2.7 mm or 1.7 mm with the agitator walls 48.

Physical vapor deposition can be carried out at essentially any desired temperature(s) over a very wide range. However, the deposited metal can be more active (perhaps due to more defects and/or lower mobility and coalescence) if the metal is deposited at relatively low temperatures (for example, at a temperature below about 150° C., preferably below about 50° C., more preferably at ambient temperature (for example, about 20° C. to about 27° C.) or less). Operating under ambient conditions can be generally preferred as being effective and economical, as no heating or chilling is required during the deposition.

The physical vapor deposition can be carried out in an inert sputtering gas atmosphere (for example, in argon, helium, xenon, radon, or a mixture of two or more thereof (preferably, argon)), and, optionally, the physical vapor deposition can be carried out in an oxidizing atmosphere. The oxidizing atmosphere preferably comprises at least one oxygen-containing gas (more preferably, an oxygen-containing gas selected from oxygen, water, hydrogen peroxide, ozone, and combinations thereof; even more preferably, an oxygen-containing gas selected from oxygen, water, and combinations thereof; most preferably, oxygen). The oxidizing atmosphere further comprises an inert sputtering gas such as argon, helium, xenon, radon, or a mixture of two or more thereof (preferably, argon). The total gas pressure (all gases) in the vacuum chamber during the PVD process can be from about 1 mTorr to about 25 mTorr (preferably, from about 5 mTorr to about 15 mTorr). The oxidizing atmosphere can comprise from about 0.05 percent to about 60 percent by weight oxygen-containing gas (preferably, from about 0.1 percent to about 50 percent by weight; more preferably, from about 0.5 percent to about 25 percent by weight), based upon the total weight of all gases in the vacuum chamber.

The diatomaceous earth support medium can optionally be calcined prior to metal deposition, although this can increase its crystalline silica content. Since gold and platinum are active right away when deposited via PVD, there is generally no need for heat treatment after metal deposition, unlike deposition by some other methodologies. Such heat treating or calcining can be carried out if desired, however, to enhance activity.

In general, thermal treatment can involve heating the support at a temperature in the range of about 125° C. to about 1000° C. for a time period in the range of about 1 second to about 40 hours, preferably about 1 minute to about 6 hours, in any suitable atmosphere such as air, an inert atmosphere such as nitrogen, carbon dioxide, argon, a reducing atmosphere such as hydrogen, and the like. The particular thermal conditions to be used can depend upon various factors including the nature of the support.

Generally, thermal treatment can be carried out below a temperature at which the constituents of the support would be decomposed, degraded, or otherwise unduly thermally damaged. Depending upon factors such as the nature of the support, the amount of metal, and the like, activity can be compromised to some degree if the system is thermally treated at too high a temperature.

Titanium Dioxide and/or Other Metal Oxides

The concentration agents comprising metal oxide can be prepared by depositing metal oxide on diatomaceous earth by hydrolysis of a hydrolyzable metal oxide precursor compound. Suitable metal oxide precursor compounds include metal complexes and metal salts that can be hydrolyzed to form metal oxides. Useful metal complexes include those comprising alkoxide ligands, hydrogen peroxide as a ligand, carboxylate-functional ligands, and the like, and combinations thereof, Useful metal salts include metal sulfates, nitrates, halides, carbonates, oxalates, hydroxides, and the like, and combinations thereof.

When using metal salts or metal complexes of hydrogen peroxide or carboxylate-functional ligands, hydrolysis can be induced by either chemical or thermal means. In chemically-induced hydrolysis, the metal salt can be introduced in the form of a solution into a dispersion of the diatomaceous earth, and the pH of the resulting combination can be raised by the addition of a base solution until the metal salt precipitates as a hydroxide complex of the metal on the diatomaceous earth. Suitable bases include alkali metal and alkaline earth metal hydroxides and carbonates, ammonium and alkyl-ammonium hydroxides and carbonates, and the like, and combinations thereof. The metal salt solution and the base solution can generally be about 0.1 to about 2 M in concentration.

Preferably, the addition of the metal salt to the diatomaceous earth is carried out with stirring (preferably, rapid stirring) of the diatomaceous earth dispersion. The metal salt solution and the base solution can be introduced to the diatomaceous earth dispersion separately (in either order) or simultaneously, so as to effect a preferably substantially uniform reaction of the resulting metal hydroxide complex with the surface of the diatomaceous earth. The reaction mixture can optionally be heated during the reaction to accelerate the speed of the reaction. In general, the amount of base added can equal the number of moles of the metal times the number of non-oxo and non-hydroxo counterions on the metal salt or metal complex.

Alternatively, when using salts of titanium or iron, the metal salt can be thermally induced to hydrolyze to form the hydroxide complex of the metal and to interact with the surface of the diatomaceous earth. In this case, the metal salt solution can generally be added to a dispersion of the diatomaceous earth (preferably, a stirred dispersion) that has been heated to a sufficiently high temperature (for example, greater than about 50° C.) to promote the hydrolysis of the metal salt. Preferably, the temperature is between about 75° C. and 100° C., although higher temperatures can be used if the reaction is carried out in an autoclave apparatus.

When using metal alkoxide complexes, the metal complex can be induced to hydrolyze to form a hydroxide complex of the metal by partial hydrolysis of the metal alkoxide in an alcohol solution. Hydrolysis of the metal alkoxide solution in the presence of diatomaceous earth can result in metal hydroxide species being deposited on the surface of the diatomaceous earth.

Alternatively, the metal alkoxide can be hydrolyzed and deposited onto the surface of the diatomaceous earth by reacting the metal alkoxide in the gas phase with water, in the presence of the diatomaceous earth. In this case, the diatomaceous earth can be agitated during the deposition in either, for example, a fluidized bed reactor or a rotating drum reactor.

After the above-described hydrolysis of the metal oxide precursor compound in the presence of the diatomaceous earth, the resulting surface-treated diatomaceous earth can be separated by settling or by filtration or by other known techniques. The separated product can be purified by washing with water and can then be dried (for example, at 50° C. to 150° C.).

Although the surface-treated diatomaceous earth generally can be functional after drying, it can optionally be calcined to remove volatile by-products by heating in air to about 250° C. to 650° C. generally without loss of function. This calcining step can be preferred when metal alkoxides are utilized as the metal oxide precursor compounds.

In general, with metal oxide precursor compounds of iron, the resulting surface treatments comprise nanoparticulate iron oxide. When the weight ratio of iron oxide to diatomaceous earth is about 0.08, X-ray diffraction (XRD) does not show the presence of a well-defined iron oxide material. Rather, additional X-ray reflections are observed at 3.80, 3.68, and 2.94 Å. TEM examination of this material shows the surface of the diatomaceous earth to be relatively uniformly coated with globular nanoparticulate iron oxide material. The crystallite size of the iron oxide material is less than about 20 nm, with most of the crystals being less than about 10 nm in diameter. The packing of these globular crystals on the surface of the diatomaceous earth is dense in appearance, and the surface of the diatomaceous earth appears to be roughened by the presence of these crystals.

In general, with metal oxide precursor compounds of titanium, the resulting surface treatments comprise nanoparticulate titania. When depositing titanium dioxide onto diatomaceous earth, XRD of the resulting product after calcination to about 350° C. can show the presence of small crystals of anatase titania. With relatively lower titanium/diatomaceous earth ratios or in cases where mixtures of titanium and iron oxide precursors are used, no evidence of anatase is generally observed by X-ray analysis.

Since titania is well-known as a potent photo-oxidation catalyst, the titania-modified diatomaceous earth concentration agents of the present invention can be used to concentrate microorganisms for analysis and then optionally also be used as photoactivatable agents for killing residual microorganisms and removing unwanted organic impurities after use. Thus, the titania-modified diatomaceous earth can both isolate biomaterials for analysis and then be photochemically cleaned for re-use. These materials can also be used in filtration applications where microorganism removal as well as antimicrobial effects can be desired.

Diatomaceous Earth

Diatomaceous earth (or kieselguhr) is a natural siliceous material produced from the remnants of diatoms, a class of ocean-dwelling microorganisms. Thus, it can be obtained from natural sources and is also commercially available (for example, from Alfa Aesar, A Johnson Matthey Company, Ward Hill, Mass.). Diatomaceous earth particles generally comprise small, open networks of silica in the form of symmetrical cubes, cylinders, spheres, plates, rectangular boxes, and the like. The pore structures in these particles can generally be remarkably uniform.

Diatomaceous earth can be used in carrying out the process of the invention as the raw, mined material or as purified and optionally milled particles. Preferably, the diatomaceous earth is in the form of milled particles with sizes in the range of about 1 micrometer to about 50 micrometers in diameter (more preferably, about 3 micrometers to about 10 micrometers).

The diatomaceous earth can optionally be heat treated prior to use to remove any vestiges of organic residues. If a heat treatment is used, it can be preferable that the heat treatment be at 500° C. or lower, as higher temperatures can produce undesirably high levels of crystalline silica.

Sample

The process of the invention can be applied to a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), a laboratory, or an area that has been potentially subjected to bioterrorism. Food processing, handling, and preparation area samples are preferred, as these are often of particular concern in regard to food supply contamination by bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be used directly or can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is a fluid (for example, a liquid, a gas, or a dispersion or suspension of solid or liquid in liquid or gas).

Examples of samples that can be used in carrying out the process of the invention include foods (for example, fresh produce or ready-to-eat lunch or "deli" meats), beverages (for example, juices or carbonated beverages), potable water, and biological fluids (for example, whole blood or a component thereof such as plasma, a platelet-enriched blood fraction, a platelet concentrate, or packed red blood cells; cell preparations (for example, dispersed tissue, bone marrow aspirates, or vertebral body bone marrow); cell suspensions; urine, saliva, and other body fluids; bone marrow; lung fluid; cerebral fluid; wound exudate; wound biopsy samples; ocular fluid; spinal fluid; and the like), as well as lysed preparations, such as cell lysates, which can be formed using known procedures such as the use of lysing buffers, and the like. Preferred samples include foods, beverages, potable water, biological fluids, and combinations thereof (with foods, beverages, potable water, and combinations thereof being more preferred).

Sample volume can vary, depending upon the particular application. For example, when the process of the invention is used for a diagnostic or research application, the volume of the sample can typically be in the microliter range (for example, 10 µL or greater). When the process is used for a food pathogen testing assay or for potable water safety testing, the volume of the sample can typically be in the milliliter to liter range (for example, 100 milliliters to 3 liters). In an industrial application, such as bioprocessing or pharmaceutical formulation, the volume can be tens of thousands of liters.

The process of the invention can isolate microorganisms from a sample in a concentrated state and can also allow the isolation of microorganisms from sample matrix components that can inhibit detection procedures that are to be used. In all of these cases, the process of the invention can be used in addition to, or in replacement of, other methods of microorganism concentration. Thus, optionally, cultures can be grown from samples either before or after carrying out the process of the invention, if additional concentration is desired.

Contacting

The process of the invention can be carried out by any of various known or hereafter-developed methods of providing contact between two materials. For example, the concentration agent can be added to the sample, or the sample can be added to the concentration agent. A dipstick coated with concentration agent can be immersed in a sample solution, a sample solution can be poured onto a film coated with concentration agent, a sample solution can be poured into a tube or well coated with concentration agent, or a sample solution can be passed through a filter (for example, a woven or nonwoven filter) coated with concentration agent.

Preferably, however, the concentration agent and the sample are combined (using any order of addition) in any of a variety of containers (optionally but preferably, a capped, closed, or sealed container; more preferably, a capped test tube, bottle, or jar). Suitable containers for use in carrying out the process of the invention will be determined by the particular sample and can vary widely in size and nature. For example, the container can be small, such as a 10 microliter container (for example, a test tube) or larger, such as a 100 milliliter to 3 liter container (for example, an Erlenmeyer flask or a polypropylene large-mouth bottle). The container, the concentration agent, and any other apparatus or additives that contact the sample directly can be sterilized (for example, by controlled heat, ethylene oxide gas, or radiation) prior to use, in order to reduce or prevent any contamination of the sample that might cause detection errors. The amount of concentration agent that is sufficient to capture or concentrate the microorganisms of a particular sample for successful detection will vary (depending upon, for example, the nature and form of the concentration agent and sample volume) and can be readily determined by one skilled in the art. For example, 10 milligrams of concentration agent per milliliter of sample can be useful for some applications.

If desired, contacting can be effected by passing a particulate concentration agent at least once through a sample (for example, by relying upon gravitational settling over a period of, for example, about 10 minutes). Contact can be enhanced by mixing (for example, by stirring, shaking, or use of a rocking platform) such that the particles of concentration agent repeatedly pass or settle through a substantial portion of the sample. For small volumes on the order of microliters (typically less than 0.5 milliliter), mixing can be rapid such as by vortexing or "nutation," for example as described in U.S. Pat. No. 5,238,812 (Coulter et al.), the description of which is incorporated herein by reference. For larger volumes on the order of greater than or equal to 0.5 milliliters (typically 0.5 milliliter to 3 liters), mixing can be achieved by gently tumbling the particulate concentration agent and the sample in an "end over end" fashion, for example as described in U.S. Pat. No. 5,576,185 (Coulter et al.), the description of which is incorporated herein by reference. Such tumbling can be accomplished, for example, by means of a device configured to hold a test tube or other type of reaction vessel and to slowly rotate the test tube or vessel in an "end over end" manner. Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes).

Thus, in carrying out the process of the invention, mixing (for example, agitation, rocking, or stirring) and/or incubation (for example, at ambient temperature) are optional but preferred, in order to increase microorganism contact with the concentration agent. A preferred contacting method includes both mixing (for example, for about 15 seconds to about 5 minutes) and incubating (for example, for about 3 minutes to about 30 minutes) a microorganism-containing sample (preferably, a fluid) with particulate concentration agent. If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, Triton™ X-100 nonionic surfactant available from Union Carbide Chemicals and Plastics, Houston, Tex.), mechanical abrasion/elution agents (for example, glass beads), and the like) can be included in the combination of concentration agent and sample.

If desired, the concentration agent (alone or in combination with, for example, antimicrobial materials and/or with carrier materials in the form of liquids (for example, water or oils), solids (for example, fabrics, polymers, papers, or inorganic solids), gels, creams, foams, or pastes) can be applied to or rubbed against a non-porous or porous, solid, microorganism-contaminated or microorganism-contaminatable material or surface (for example, for use as a "cleaning" agent). Binders, stabilizers, surfactants, or other property modifiers can be utilized, if desired.

For such use, the concentration agent can be applied to woven or nonwoven fabrics and can be applied to disposable surfaces such as paper, tissues, cotton swabs, as well as to a variety of absorbent and nonabsorbent materials. For example, the concentration agent can be incorporated into cloth or paper carrier materials for use as "cleaning" wipes.

The concentration agent can be applied (for example, in the form of wipes or pastes comprising a carrier material) to solid surfaces, for example, in home, day-care, industrial, and hospital settings, for cleansing toys, equipment, medical devices, work surfaces, and the like. When used for cleansing or other purposes, the sample can be simultaneously collected and contacted with the concentration agent in a single step, if desired.

Segregation and/or Separation

Optionally but preferably, the process of the invention further comprises segregation of the resulting microorganism-bound concentration agent. Such segregation preferably can be achieved by relying, at least in part, upon gravitational settling (gravity sedimentation; for example, over a time period of about 5 minutes to about 30 minutes). In some cases, however, it can be desirable to accelerate segregation (for example, by centrifugation or filtration) or to use combinations of any of the segregation methods.

The process of the invention can optionally further comprise separating the resulting microorganism-bound concentration agent and the sample. For fluid samples, this can involve removal or separation of the supernatant that results upon segregation. Separation of the supernatant can be carried out by numerous methods that are well-known in the art (for example, by decanting or siphoning, so as to leave the microorganism-bound concentration agent at the bottom of the container or vessel utilized in carrying out the process).

The process of the invention can be carried out manually (for example, in a batch-wise manner) or can be automated (for example, to enable continuous or semi-continuous processing).

Detection

A variety of microorganisms can be concentrated and, optionally but preferably, detected by using the process of the invention, including, for example, bacteria, fungi, yeasts, protozoans, viruses (including both non-enveloped and enveloped viruses), bacterial endospores (for example, *Bacillus* (including *Bacillus anthracis*, *Bacillus cereus*, and *Bacillus subtilis*) and *Clostridium* (including *Clostridium botulinum*, *Clostridium difficile*, and *Clostridium perfringens*)), and the like, and combinations thereof (preferably, bacteria, yeasts, viruses, bacterial endospores, fungi, and combinations thereof; more preferably, bacteria, yeasts, viruses, bacterial endospores, and combinations thereof; even more preferably, bacteria, viruses, bacterial endospores, and combinations thereof; most preferably, gram-negative bacteria, gram-positive bacteria, non-enveloped viruses (for example, norovirus, poliovirus, hepatitis A virus, rhinovirus, and combinations thereof), bacterial endospores, and combinations thereof). The process has utility in the detection of pathogens, which can be important for food safety or for medical, environmental, or anti-terrorism reasons. The process can be particularly useful in the detection of pathogenic bacteria (for example, both gram negative and gram positive bacteria), as well as various yeasts, molds, and mycoplasmas (and combinations of any of these).

Genera of target microorganisms to be detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof. Samples can contain a plurality of microorganism strains, and any one strain can be detected independently of any other strain. Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans, Staphylococcal enterotoxin* ssp, *Bacillus cereus, Bacillus anthracis, Bacillus atrophaeus, Bacillus subtilis, Clostridium perfringens, Clostridium botulinum, Clostridium difficile, Enterobacter sakazakii, Pseudomonas aeruginosa*, and the like, and combinations thereof (preferably, *Staphylococcus aureus, Salmonella enterica, Saccharomyces cerevisiae, Bacillus atrophaeus, Bacillus subtilis, Escherichia coli*, human-infecting non-enveloped enteric viruses for which *Escherichia coli* bacteriophage is a surrogate, and combinations thereof).

Microorganisms that have been captured or bound (for example, by adsorption) by the concentration agent can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.), the descriptions of which are incorporated herein by reference.

Since the process of the invention is non-strain specific, it provides a general capture system that allows for multiple microorganism strains to be targeted for assay in the same sample. For example, in assaying for contamination of food samples, it can be desired to test for *Listeria monocytogenes, Escherichia coli,* and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

Diagnostic Kit

A diagnostic kit for use in carrying out the process of the invention comprises (a) an above-described concentration agent (preferably, particulate); and (b) a testing container (preferably, a sterile testing container) for use in carrying out the process of the invention. Preferably, the diagnostic kit further comprises one or more components selected from microorganism culture or growth media, lysis reagents, buffers, bioluminescence detection assay components (for example, luminometer, lysis reagents, luciferase enzyme, enzyme substrate, reaction buffers, and the like), genetic detection assay components, instructions for carrying out the process, and combinations thereof. A preferred lysis reagent is a lytic enzyme supplied in a buffer, and preferred genetic detection assay components include one or more primers specific for a target microorganism.

For example, a preferred embodiment of the diagnostic kit of the invention contains a particulate concentration agent (for example, in a sterile disposable container such as a glass or polypropylene vial), in combination with instructions for using said agent in carrying out the process of the invention (for example, by mixing the concentration agent with a fluid sample to be analyzed, allowing the concentration agent to settle by gravity, removing the resulting supernatant, and detecting the presence of at least one concentration agent-bound target microorganism strain). The concentration agent optionally can be hydrated in a small volume of buffer with preservative to improve stability during storage and transportation and/or can be contained/aliquotted in a tear-open, sealed pouch to prevent contamination. The concentration agent can be in the form of a dispersion or suspension in a liquid or can be in powder form. Preferably, the diagnostic kit comprises pre-measured aliquots (for example, based upon sample volume) of particulate concentration agent (more preferably, contained in one or more tear-open, sealed pouches).

EXAMPLES

Objects and advantages of this invention are further illustrated by the following examples, but the particular materials and amounts thereof recited in these examples, as well as other conditions and details, should not be construed to unduly limit this invention.

Materials

Kieselguhr (diatomaceous earth) was purchased from Alfa Aesar (A Johnson Matthey Company, Ward Hill, Mass.) as a white powder (325 mesh; all particles less than 44 micrometers in size). This material was shown by X-ray diffraction (XRD) to contain amorphous silica along with crystalline α-cristobalite and quartz. Calcined diatomaceous earth was purchased from Solvadis, GmbH, Frankfurt, Germany (and observed to comprise small rods about 5 to about 80 micrometers in length and about 3 to about 8 micrometers in width, along with porous disks and disk fragments up to about 60 micrometers in primary length and asymmetrical fragments about 3 to about 60 micrometers in primary length). This material was shown by XRD to comprise predominantly α-cristobalite.

All microorganism cultures were purchased from The American Type Culture Collection (ATCC; Manassas, Va.).

Concentration agents comprising various different surface modifiers (namely, titanium dioxide; titanium dioxide in combination with ferric oxide; platinum; gold; and gold in combination with ferric oxide) were prepared by surface treating the diatomaceous earth in the manner described below:

Gold Deposition

About 57-60 g of dried diatomaceous earth or metal oxide-modified diatomaceous earth support media (about 300 mL volume of powder) was further dried in an oven at 150° C. for 24 hours to remove residual water. The resulting dried sample was placed while hot into the PVD apparatus described above in the detailed description with the PVD apparatus having a particle agitator with a blade gap of 2.7 mm. The vacuum chamber of the apparatus was then evacuated to a background pressure of about $5 \times 10^{-5}$ Torr, and gas comprising argon sputtering gas was admitted to the chamber at a pressure of about 10 mTorr.

The metal deposition process was then carried out by applying power to the cathode of the apparatus for a pre-set period of time, with its particle agitator shaft and holed blades being rotated at 4 rpm during DC magnetron sputter coating of metal at a controlled power of 0.02 kW. The duration of sputter coating was 5 hours. After the sputter coating was completed, the vacuum chamber was vented with air to ambient conditions, and the resulting metal-coated sample was removed from the PVD apparatus and sieved through a 25 mesh (0.707 mm) screen to separate fine particulates generated during the process. The amount of metal that had been deposited on the sample was determined by weighing (both before and after the deposition process) the metal sputtering target that was utilized. In general, about 18 percent of the weight loss of the target represented metal deposited on the sample (based on inductively coupled plasma analysis). From this information, the resulting amount of gold on the support medium was calculated to be about 0.9 weight percent.

Platinum Deposition

The above-described gold deposition process was essentially repeated, with the exception that a 7.62-cm (3-inch)

platinum target was substituted for the 7.62-cm (3-inch) gold target that had been used, the power was set at 0.03 kW, and the time of deposition was 1 hour. The resulting amount of platinum on the support medium was calculated to be about 0.25 weight percent.

Deposition of Titanium Dioxide

A 20 weight percent titanium (IV) oxysulfate dehydrate solution was prepared by dissolving 20.0 g of $TiO(SO_4)$ .$2H_2O$ (Noah Technologies Corporation, San Antonio, Tex.) in 80.0 g of deionized water with stirring. 50.0 g of this solution was mixed with 175 mL of deionized water to form a titanium dioxide precursor compound solution. A dispersion of diatomaceous earth was prepared by dispersing 50.0 g of diatomaceous earth in 500 mL of deionized water in a large beaker with rapid stirring. After heating the diatomaceous earth dispersion to about 80° C., the titanium dioxide precursor compound solution was added dropwise while rapidly stirring over a period of about 1 hour. After the addition, the beaker was covered with a watch glass and its contents heated to boiling for 20 minutes. An ammonium hydroxide solution was added to the beaker until the pH of the contents was about 9. The resulting product was washed by settling/decantation until the pH of the wash water was neutral. The product was separated by filtration and dried overnight at 100° C.

A portion of the dried product was placed into a porcelain crucible and calcined by heating from room temperature to 350° C. at a heating rate of about 3° C. per minute and then held at 350° C. for 1 hour.

Deposition of Iron Oxide

Iron oxide was deposited onto diatomaceous earth using essentially the above-described titanium dioxide deposition process, with the exception that a solution of 20.0 g of $Fe(NO_3)_3.9H_2O$ (J. T. Baker, Inc., Phillipsburg, N.J.) dissolved in 175 mL of deionized water was substituted for the titanyl sulfate solution. A portion of the resulting iron oxide-modified diatomaceous earth was similarly calcined to 350° C. for further testing.

Deposition of Iron Oxide and Titanium Dioxide

A mixture of iron oxide and titanium dioxide was deposited onto diatomaceous earth using essentially the above-described titanium dioxide deposition process, with the exception that a solution of 10.0 g of $Fe(NO_3)_3.9H_2O$ (J. T. Baker, Inc., Phillipsburg, N.J.) and 25.0 g of $TiO(SO_4).2H_2O$ (Noah Technologies Corporation, San Antonio, Tex.) dissolved in 175 mL of deionized water was substituted for the titanyl sulfate solution. A portion of the resulting iron oxide- and titanium dioxide-modified diatomaceous earth was similarly calcined to 350° C. for further testing.

Microorganism Concentration Test Method

An isolated microorganism colony was inoculated into 5 mL BBL™ Trypticase™ Soy Broth (Becton Dickinson, Sparks, Md.) and incubated at 37° C. for 18-20 hours. This overnight culture at ~$10^9$ colony forming units per mL was diluted in adsorption buffer (containing 5 mM KCl, 1 mM $CaCl_2$, 0.1 mM $MgCl_2$, and 1 mM $K_2HPO_4$) at pH 7.2 to obtain $10^3$ microorganisms per mL dilution. A 1.1 mL volume of the microorganism dilution was added to separate, labeled sterile 5 mL polypropylene tubes (BD Falcon™, Becton Dickinson, Franklin Lakes, N.J.) containing 10 mg of concentration agent, each of which was capped and mixed on a Thermolyne Maximix Plus™ vortex mixer (Barnstead International, Iowa). Each capped tube was incubated at room temperature (25° C.) for 15 minutes on a Thermolyne Vari Mix™ shaker platform (Barnstead International, Iowa). After the incubation, each tube was allowed to stand on the lab bench for 10 minutes to settle the concentration agent. Control sample tubes containing 1.1 mL of the microorganism dilution without concentration agent were treated in the same manner. The resulting settled concentration agent and/or supernatant (and the control samples) were then used for analysis.

The settled concentration agent was re-suspended in 1 mL sterile Butterfield's Buffer solution (pH 7.2±0.2; monobasic potassium phosphate buffer solution; VWR Catalog Number 83008-093, VWR, West Chester, Pa.) and plated on 3M™ Petrifilm™ Aerobic Count Plates culture medium (dry, rehydratable; 3M Company, St. Paul., Minn.) according to the manufacturer's instructions. Aerobic count was quantified using a 3M™ Petrifilm™ Plate Reader (3M Company, St. Paul., Minn.). Results were calculated using the following formula:

Percent CFU/mL in Re-suspended Concentration Agent=(number of colonies from plated re-suspended concentration agent)/(number of colonies from plated untreated control sample)×100

(where CFU=Colony Forming Unit, which is a unit of live or viable microorganisms). Results were then reported in terms of percent capture of microorganisms by the concentration agent using the formula below:

Capture Efficiency or Percent Capture=Percent CFU/mL in Re-suspended Concentration Agent For comparison purposes, in at least some cases 1 mL of the supernatant was removed and plated undiluted or diluted 1:10 in Butterfield's Buffer solution and plated onto 3M™ Petrifilm™ Aerobic Count Plates culture medium. Aerobic count was quantified using a 3M™ Petrifilm™ Plate Reader (3M Company, St. Paul., Minn.). Results were calculated using the following formula:

Percent CFU/mL in Supernatant=(number of colonies from plated supernatant)/(number of colonies from plated untreated control sample)×100

(where CFU=Colony Forming Unit, which is a unit of live or viable microorganisms). When the microorganism colonies and the concentration agent were similar in color (providing little contrast for the plate reader), results were based upon the supernatant and were then reported in terms of percent capture of microorganisms by the concentration agent using the formula below:

Capture Efficiency or Percent Capture=100−Percent CFU/mL in Supernatant

Examples 1-12 and Comparative Examples 1 and 2

Using the above-described microorganism concentration test method, 10 mg of various different surface-treated diatomaceous earth or surface-treated calcined diatomaceous earth concentration agents (prepared as described above) and 10 mg of untreated diatomaceous earth (hereinafter, DE) were tested separately for bacterial concentration against target microorganisms, the gram-negative bacterium *Salmonella enterica* subsp. *enterica serovar Typhimurium* (ATCC 35987) and the gram-positive bacterium *Staphylococcus aureus* (ATCC 6538). The results are shown in Table 1 below.

TABLE 1

| Example No. | Microorganism | Concentration Agent | Percent Capture ± Standard Deviation |
|---|---|---|---|
| C-1 | *Staphylococcus* | DE | 54 ± 13 |
| 1 | *Staphylococcus* | $TiO_2$-DE | 94 ± 4 |
| 2 | *Staphylococcus* | $Fe_2O_3$—$TiO_2$-DE | 96 ± 1 |

TABLE 1-continued

| Example No. | Microorganism | Concentration Agent | Percent Capture ± Standard Deviation |
|---|---|---|---|
| 3 | Staphylococcus | calcined $Fe_2O_3$—$TiO_2$-DE | 100 ± 0 |
| 4 | Staphylococcus | Pt-calcined DE | 99 ± 0 |
| 5 | Staphylococcus | Au—$Fe_2O_3$-DE | 99 ± 0 |
| 6 | Staphylococcus | Au-calcined DE | 99 ± 0 |
| C-2 | Salmonella | DE | 45 ± 1 |
| 7 | Salmonella | $TiO_2$-DE | 86 ± 3 |
| 8 | Salmonella | $Fe_2O_3$—$TiO_2$-DE | 88 ± 1 |
| 9 | Salmonella | calcined $Fe_2O_3$—$TiO_2$-DE | 89 ± 5 |
| 10 | Salmonella | Pt-calcined DE | 72 ± 1 |
| 11 | Salmonella | Au—$Fe_2O_3$-DE | 91 ± 6 |
| 12 | Salmonella | Au-calcined DE | 100 ± 0 |
| 13 | Salmonella | Au-DE | 89 ± 2 |

Examples 14-19 and Comparative Example 3

Using the above-described microorganism concentration test method, 10 mg of various different surface-treated diatomaceous earth or surface-treated calcined diatomaceous earth concentration agents (prepared as described above) and 10 mg of untreated diatomaceous earth (hereinafter, DE) were tested separately for yeast concentration of the target microorganism, Saccharomyces cerevisiae ($10^2$ CFU/mL; ATCC 201390). The resulting materials were plated on 3M™ Petrifilm™ Yeast and Mold Count Plate culture medium (dry, rehydratable; 3M Company, St. Paul, Minn.) and incubated for 5 days according to the manufacturer's instructions. Isolated yeast colonies were counted manually, and percent capture was calculated as described above. The results are shown in Table 2 below (standard deviation for all samples less than 10 percent).

TABLE 2

| Example No. | Microorganism | Concentration Agent | Percent Capture |
|---|---|---|---|
| C-3 | Saccharomyces | DE | 42 |
| 14 | Saccharomyces | $TiO_2$-DE | 99 |
| 15 | Saccharomyces | $Fe_2O_3$—$TiO_2$-DE | 93 |
| 16 | Saccharomyces | calcined $Fe_2O_3$—$TiO_2$-DE | 100 |
| 17 | Saccharomyces | Pt-calcined DE | 100 |
| 18 | Saccharomyces | Au—$Fe_2O_3$-DE | 100 |
| 19 | Saccharomyces | Au-calcined DE | 99 |

Examples 20-22 and Comparative Examples 4-6

Food samples were purchased from a local grocery store (Cub Foods, St. Paul). Ham slices, lettuce, and apple juice samples (11 g) were weighed in sterile glass dishes and added to sterile Stomacher™ polyethylene filter bags (Seward Corp, Norfolk, UK). The food samples were spiked with bacterial cultures at a $10^2$ CFU/mL concentration using an 18-20 hour overnight culture (stock) of Salmonella enterica subsp. enterica serovar Typhimurium (ATCC 35987). This was followed by the addition of 99 mL of Butterfield's Buffer solution to each spiked sample. The resulting samples were blended for a 2-minute cycle in a Stomacher™ 400 Circulator laboratory blender (Seward Corp. Norfolk, UK). The blended samples were collected in sterile 50 mL conical polypropylene centrifuge tubes (BD Falcon™, Becton Dickinson, Franklin Lakes, N.J.) and centrifuged (Eppendorf™ centrifuge 5804; Westbury, N.Y.) at 2000 revolutions per minute (rpm) for 5 minutes to remove large debris. The resulting supernatants were used as samples for further testing.

Using the above-described microorganism concentration test method, each 1 mL test sample prepared as above was added separately to a test tube containing 10 mg of surface-treated diatomaceous earth and to a control test tube containing 10 mg of untreated diatomaceous earth and tested for bacterial concentration of the target microorganism, Salmonella enterica subsp. enterica serovar Typhimurium (ATCC 35987). For testing in lettuce, samples were placed in sterile 100×20 mm tissue culture petridishes (Sarstedt, Newton, N.C.) and incubated under ultraviolet (UV) lights in an AlphaImager™ MultiImage™ light cabinet (Alpha Innotech Corporation, San Leandro, Calif.) for 1 hour to eliminate background flora. Such UV-treated samples were confirmed for absence of native flora (by plating and counting a 1 mL sample essentially as described above) and then used for concentration experiments. The results are shown in Table 3 below (standard deviation for all samples less than 10 percent).

TABLE 3

| Example No. | Microorganism | Concentration Agent | Sample | Percent Capture |
|---|---|---|---|---|
| C-4 | Salmonella | DE | Apple Juice | 43 |
| 20 | Salmonella | Au—$Fe_2O_3$-DE | Apple Juice | 94 |
| C-5 | Salmonella | DE | Ham | 75 |
| 21 | Salmonella | Au—$Fe_2O_3$-DE | Ham | 94 |
| C-6 | Salmonella | DE | Lettuce | 55 |
| 22 | Salmonella | Au—$Fe_2O_3$-DE | Lettuce | 80 |

Examples 23-24 and Comparative Examples 7-8

Following the procedure of Examples 20-22 and Comparative Examples 4-6 above with a turkey sample (using 25 g of sliced turkey and 225 mL Butterfield's Buffer solution), surface treated diatomaceous earth and untreated diatomaceous earth were separately tested for concentration of the target microorganism Salmonella enterica subsp. enterica serovar Typhimurium (ATCC 35987) from large-volume samples (300 mg concentration agent per 30 mL sample volume). Also tested was potable water (100 mL) from a drinking fountain, which was collected in a sterile 250 mL glass bottle (VWR, West Chester, Pa.) and inoculated with the target microorganism Salmonella enterica subsp. enterica serovar Typhimurium (ATCC 35987) at $10^2$ CFU/mL. The resulting inoculated water was mixed manually end-to-end 5 times and incubated at room temperature (25° C.) for 15 minutes.

30 mL samples prepared as described above were added to sterile 50 mL conical polypropylene centrifuge tubes (BD Falcon™, Becton Dickinson, Franklin Lakes, N.J.) containing 300 mg of concentration agent and were tested by using the above-described microorganism concentration test method. The resulting settled concentration agent was resuspended in 30 mL sterile Butterfield's Buffer solution and plated on 3M™ Petrifilm™ Aerobic Count Plates culture medium. The results are shown in Table 4 below (standard deviation for all samples less than 10 percent).

TABLE 4

| Example No. | Microorganism | Concentration Agent | Sample | Percent Capture |
|---|---|---|---|---|
| C-7 | Salmonella | DE | Potable Water | 79 |
| 23 | Salmonella | Au—Fe$_2$O$_3$-DE | Potable Water | 97 |
| C-8 | Salmonella | DE | Turkey | 52 |
| 24 | Salmonella | Au—Fe$_2$O$_3$-DE | Turkey | 88 |

Examples 25-32

10 mg samples of various different surface-treated diatomaceous earth concentration agents (prepared as described above) were tested separately for concentration of the target bacterial endospores Bacillus atrophaeus (ATCC 9372) and Bacillus subtilis (ATCC 19659). The above-described microorganism concentration test method was utilized with the following modifications: the overnight cultures had 1.4×10$^3$ CFU/mL Bacillus atrophaeus and 6×10$^2$ CFU/mL Bacillus subtilis, respectively; the resulting supernatants were plated undiluted; and the settled concentration agent with bound microorganism was resuspended in 5 mL sterile Butterfield's Buffer solution and plated in duplicate (1 mL each). Capture efficiencies were calculated based on counts from the plated supernatants, and the results are shown in Table 5 below (standard deviation for all samples less than 10 percent).

TABLE 5

| Example No. | Microorganism | Concentration Agent | Percent Capture |
|---|---|---|---|
| 25 | Bacillus atrophaeus | TiO$_2$-DE | 79 |
| 26 | Bacillus atrophaeus | Pt-DE | 100 |
| 27 | Bacillus atrophaeus | Au-DE | 81 |
| 28 | Bacillus atrophaeus | Au—Fe$_2$O$_3$-DE | 100 |
| 29 | Bacillus subtilis | TiO$_2$-DE | 97 |
| 30 | Bacillus subtilis | Pt-DE | 100 |
| 31 | Bacillus subtilis | Au-DE | 99 |
| 32 | Bacillus subtilis | Au—Fe$_2$O$_3$-DE | 99 |

Examples 33-36

10 mg samples of two different surface-treated diatomaceous earth concentration agents (namely, Pt-DE and Au—Fe$_2$O$_3$-DE) were tested separately for concentration of the target non-enveloped, bacteria-infecting virus, Escherichia coli bacteriophage MS2 (ATCC 15597-B1; which is often used as a surrogate for various human-infecting, non-enveloped enteric viruses). A double layer agar method (described below) was used to assay for capture of the Escherichia coli bacteriophage MS2 (ATCC 15597-B1) using Escherichia coli bacteria (ATCC 15597) as host.

Escherichia coli bacteriophage MS2 stock was diluted ten-fold serially in sterile 1× adsorption buffer (containing 5 mM KCl, 1 mM CaCl$_2$, 0.1 mM MgCl$_2$, and 1 mM K$_2$HPO$_4$) at pH 7.2 to obtain two dilutions with 10$^3$ and 10$^2$ plaque forming units per milliliter (PFUs/mL), respectively. A 1.0 mL volume of resulting bacteriophage dilution was added to a labeled sterile 5 mL polypropylene tube (BD Falcon™, Becton Dickinson, Franklin Lakes, N.J.) containing 10 mg of concentration agent and mixed on a Thermolyne Maximix Plus™ vortex mixer (Barnstead International, Iowa). The capped tube was incubated at room temperature (25° C.) for 15 minutes on a Thermolyne Vari Mix™ shaker platform (Barnstead International, Iowa). After the incubation, the tube was allowed to stand on the lab bench for 10 minutes to settle the concentration agent. A control sample tube containing 1.0 mL of the bacteriophage dilution without concentration agent was treated in the same manner. The resulting settled concentration agent and supernatant (and the control sample) were then used for analysis.

100 microliters of the supernatant was removed and assayed for bacteriophage using the double layer agar method described below. An additional 800 microliters of supernatant was removed and discarded. One hundred microliters of the settled concentration agent was also assayed for bacteriophage.

Double Layer Agar Method:

A single colony of Escherichia coli bacteria (ATCC 15597) was inoculated into 25 mL sterile 3 weight percent tryptic soy broth (Bacto™ Tryptic Soy Broth, Becton Dickinson and Company, Sparks, Md.; prepared according to manufacturer's instructions) and incubated at 37° C. in a shaker incubator (Innova™ 44, New Brunswick Scientific Co., Inc., Edison, N.J.) set at 250 revolutions per minute (rpm) overnight. 750 microliters of this overnight culture was used to inoculate 75 mL sterile 3 weight percent tryptic soy broth. The resulting culture was incubated at 37° C. in the shaker incubator set at 250 rpm to obtain Escherichia coli cells in the exponential phase as measured by absorbance at 550 nm (absorbance values 0.3-0.6) using a SpectraMax M5 spectrophotometer (Molecular Devices, Sunnyvale, Calif.). The cells were incubated on ice until used for assay.

One hundred microliters of the above-described bacteriophage test samples were mixed with 75 microliters of the ice-incubated Escherichia coli (host bacteria) cells and incubated at room temperature (25° C.) for 5 minutes. The resulting samples were mixed with 5 mL sterile molten top agar (3 weight percent tryptic soy broth, 1.5 weight percent NaCl, 0.6 weight percent agar; prepared that day and maintained in a 48° C. waterbath). The mixture was then poured on top of bottom agar (3 weight percent tryptic soy broth, 1.5 weight percent NaCl, 1.2 weight percent agar) in petridishes. The molten agar component of the mixture was allowed to solidify for 5 minutes, and the petridishes or plates were inverted and incubated at 37° C. The plates were visually inspected after overnight incubation, and those plates containing settled concentration agent (as well as the control plate) showed the presence of bacteriophage plaques. Capture efficiencies were calculated based on counts from the plated supernatants and determined to be 96 percent and 97 percent for Pt-DE (for the 10$^3$ and 10$^2$ PFU/mL dilutions, respectively) and 94 percent and 95 percent for Au—Fe$_2$O$_3$-DE (for the 10$^3$ and 10$^2$ PFU/mL dilutions, respectively) (standard deviation less than 10 percent).

Examples 37-38

Apple juice was purchased from a local grocery store (Cub Foods, St. Paul). Apple juice (11 g) was weighed in a sterile glass dish and added to 99 mL sterile Butterfield's Buffer. The resulting combination was mixed by swirling for 1 minute and was spiked with two bacterial cultures, each at a 1 CFU/mL concentration, using 18-20 hour overnight cultures (bacterial stocks) of Salmonella enterica subsp. enterica serovar Typhimurium (ATCC 35987) and Escherichia coli (ATCC 51813). Serial dilutions of the bacterial stocks had been made in 1× adsorption buffer as described above. Using the above-described microorganism concentration test method, a 10 mL volume of the spiked apple juice sample was added to a sterile 50 mL conical polypropylene centrifuge tube (BD Falcon™, Becton Dickinson, Franklin Lakes, N.J.) containing 100 mg of a surface-treated diatomaceous earth concentration agent (namely, $TiO_2$-DE or Au—$Fe_2O_3$-DE) and incubated for 15 minutes for bacterial capture/concentration of the target microorganism, *Salmonella* (in the presence of the *Escherichia coli*, a competitor microorganism). The resulting supernatant was removed, and the settled concentration agent was transferred to another sterile 50 mL tube containing 2 mL sterile 3 weight percent tryptic soy broth (Bacto™ Tryptic Soy Broth, Becton Dickinson and Company, Sparks, Md.; prepared according to manufacturer's instructions). The tube was loosely capped, and its contents were mixed and incubated at 37° C. After overnight incubation, the resulting broth mixture was tested for the presence of *Salmonella* using a RapidChek™ *Salmonella* lateral flow immunoassay test strip from SDI (Strategic Diagnostics, Inc., Newark, Del.). Visual inspection of the test strip showed it to be positive for *Salmonella*.

Nucleic acid detection by polymerase chain reaction (PCR) was also carried out for the microorganism-containing broth mixture. 1 mL of the above-described overnight-incubated, concentration agent-containing broth was assayed as a test sample for the presence of *Salmonella* by using a TaqMan™ ABI *Salmonella enterica* Detection Kit from Applied Biosystems (Foster City, Calif.). As a control sample, 1 mL of the 18-20 hour overnight culture (stock) of *Salmonella enterica* subsp. *enterica serovar Typhimurium* (ATCC 35987) was also assayed. PCR testing was conducted in a Stratagene Mx3005P™ QPCR (quantitative PCR) System (Stratagene Corporation, La Jolla, Calif.) by using the following cycle conditions per cycle for 45 cycles: 25° C. for 30 seconds, 95° C. for 10 minutes, 95° C. for 15 seconds, and 60° C. for 1 minute. An average (n=2) cycle threshold value (CT value) of 17.71 was obtained for the control sample. Average (n=2) CT values of 20.44 and 16.53 were obtained for the test samples containing $TiO_2$-DE or Au—$Fe_2O_3$-DE, respectively, indicating a positive PCR reaction and confirming the presence of *Salmonella*.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A concentration agent comprising a particulate support selected from diatomaceous earth, metal oxide-modified diatomaceous earth, and combinations thereof, the particulate support bearing, on at least a portion of its surface, a surface treatment comprising titanium dioxide, fine-nanoscale gold or platinum, or a combination thereof, wherein when the surface treatment is fine-nanoscale gold or platinum or a combination thereof, at least a portion of the surface treatment has all dimensions in the range of up to 3 nanometers, wherein the concentration agent comprises a negative zeta potential when suspended in water.

2. The concentration agent of claim 1, wherein the surface treatment is titanium dioxide.

3. The concentration agent of claim 1, wherein the surface treatment is fine-nanoscale gold or platinum, or a combination thereof.

4. The concentration agent of claim 1, wherein the metal oxide of the metal oxide-modified diatomaceous earth is selected from ferric oxide, titanium dioxide, zinc oxide, aluminum oxide, and combinations thereof; with the proviso that if the metal oxide is titanium dioxide, then the surface treatment is fine-nanoscale gold or platinum, or a combination thereof.

5. An article comprising the concentration agent of claim 1 having at least one microorganism strain bound to the concentration agent.

6. A method of making a concentration agent according to claim 2, the method comprising:
   (a) providing a particulate support selected from diatomaceous earth, metal oxide-modified diatomaceous earth, and combinations thereof;
   (b) providing a precursor compound comprising a hydrolysable titanium dioxide precursor;
   (c) combining the particulate support and the precursor compound; and
   (d) hydrolyzing the precursor compound such that titanium dioxide is deposited on the particulate support.

7. The method of claim 6, further comprising heating the particulate support having the titanium dioxide deposited thereon at a temperature in a range from 250° C. to 650° C.

8. The method of claim 6, wherein the metal oxide of the metal oxide-modified diatomaceous earth is selected from ferric oxide, zinc oxide, aluminum oxide, and combinations thereof.

9. A method of making a concentration agent according to claim 3, the method comprising:
   (a) providing a particulate support selected from diatomaceous earth, metal oxide-modified diatomaceous earth, and combinations thereof; and
   (b) depositing fine-nanoscale gold or platinum on the particulate support by physical deposition.

10. The method of claim 9, wherein the metal oxide of the metal oxide-modified diatomaceous earth is selected from ferric oxide, titanium dioxide, zinc oxide, aluminum oxide, and combinations thereof; with the proviso that if the metal oxide is titanium dioxide, then the surface treatment is fine-nanoscale gold or platinum, or a combination thereof.

11. The concentration agent of claim 3, wherein at least a portion of the surface treatment comprises ultra-nanoscale gold.

12. The concentration agent of claim 11, wherein at least a portion of the surface treatment has all dimensions in the range of less than 1.5 nanometers.

13. The concentration agent of claim 1, wherein the diatomaceous earth comprises diatomaceous earth from which organic residues have been removed.

14. The concentration agent of claim 1, wherein the diatomaceous earth comprises diatomaceous earth from which residual water has been removed.

* * * * *

UNITED STATES PATENT AND TRADEMARK OFFICE
CERTIFICATE OF CORRECTION

PATENT NO. : 8,951,575 B2  Page 1 of 1
APPLICATION NO. : 14/023782
DATED : February 10, 2015
INVENTOR(S) : Manjiri Kshirsagar It is certified that error appears in the above-identified patent and that said Letters Patent is hereby corrected as shown below:

In the Specification

Column 1,
Line 9, delete "Oct. 10, 2008," and insert -- Oct. 2, 2008 --, therefor.

Column 17,
Line 43, delete "$TiO(SO_4).{_2}H_2O$" and insert -- $iO(SO_4).2H_2O$ --, therefor.

Column 20,
Line 14, delete "MultiImage™" and insert -- MultiImage™ --, therefor.

Signed and Sealed this
Seventh Day of July, 2015

Michelle K. Lee
*Director of the United States Patent and Trademark Office*